United States Patent [19]

Ferdinandi et al.

[11] Patent Number: 4,748,252

[45] Date of Patent: May 31, 1988

[54] SUBSTITUTED 1,3,4,9-TETRAHYDROPYRANO[3,4-B]INDOLE-1-ACETIC ACIDS

[75] Inventors: Eckhardt S. Ferdinandi, Princeton; Dominick Mobilio, Plainsboro; Joseph P. Sabatucci, Plainsboro; Leslie G. Humber, North Brunswick, all of N.J.

[73] Assignee: American Home Products Corporation, New York, N.Y.

[21] Appl. No.: 7,876

[22] Filed: Jan. 28, 1987

Related U.S. Application Data

[62] Division of Ser. No. 896,998, Aug. 15, 1986, Pat. No. 4,686,213.

[51] Int. Cl.[4] ............................................ C07D 493/04
[52] U.S. Cl. ................................... 548/432; 548/495; 548/507
[58] Field of Search ........................ 548/432, 495, 507

[56] References Cited

U.S. PATENT DOCUMENTS

| 3,843,681 | 10/1974 | Demerson et al. | 548/432 |
| 3,939,178 | 2/1976 | Demerson et al. | 548/432 |
| 3,974,179 | 8/1976 | Demerson et al. | 548/432 |
| 4,585,877 | 4/1986 | Demerson et al. | 548/432 |

OTHER PUBLICATIONS

M. Cayen et al., Chem. Abstracts, vol. 96, No. 170n (1982), The Metabolic Disposition of Etodolac in Rats, Dogs and Man.
C. Demerson et al., J. Med. Chem., 18, 189 (1975).

*Primary Examiner*—Mary E. Ceperley
*Attorney, Agent, or Firm*—Walter Patton

[57] ABSTRACT

Indole derivatives characterized by having a 1,3,4,9-tetrahydropyrano[3,4-b]indole-1-acetic acid nucleus bearing a substituent in position 1 and 4. The nucleus may be optionally substituted at position 8. The derivatives are useful anti-inflammatory and analgesic agents and methods and chemical intermediates for their preparation are also disclosed.

3 Claims, No Drawings

SUBSTITUTED 1,3,4,9-TETRAHYDROPYRANO[3,4-B]INDOLE-1-ACETIC ACIDS

This is a division of copending application Ser. No. 896,998 filed Aug. 15, 1986 now U.S. Pat. No. 4,686,213.

BACKGROUND OF THE INVENTION a. Field of Invention

This invention relates to novel indole derivatives, and to the processes for their preparation and use. Included are useful chemical intermediates for the preparation of said indole derivatives.

More specifically, this invention relates to tricyclic acetic acid derivatives in which the tricyclic portion thereof is characterized by having an indole portion fused to a pyrano ring. Still more specifically, the compounds of this invention are characterized as derivatives of the following tricyclic acetic acid system:

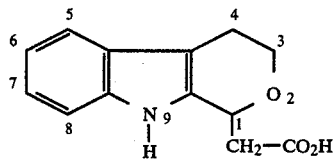

1,3,4,9-tetrahydropyrano[3,4-b]indole-1-acetic acid in which the carbons at the 1-, and 4-position, and optionally at the 8-position are further substituted.

The indole derivatives of this invention have been found to exhibit useful pharmacodynamic properties without eliciting undesirable side effects. Notable attributes of these compounds are their anti-inflammatory and analgesic activities.

b. Prior Art

The relevant prior art to the present invention is:

Katz et al, U.S. Ser. No. 838,510, filed Mar. 11, 1986 now U.S. Pat. No. 4,670,462. Katz et al disclosed 1,3,4,9-tetrahydropyrano[3,4-b]indoles having analgesic and anti-inflammatory activity but with substituents differing from those of the present invention. Related U.S. Patents are Nos. 3,939,178; 3,974,179 and 3,843,681. C. Demerson et al, J. Med. Chem. 18, 189 (1975) disclosed the chemistry and anti-inflammatory activity of related 1,3,4,9-tetrahydropyrano[3,4-b]indole-1-alkanoic acids.

SUMMARY OF THE INVENTION

The compounds and chemical intermediates of this invention are represented by formula (I)

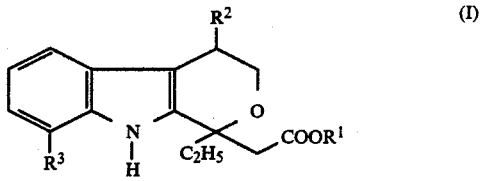

wherein $R^1$ is —H or lower alkyl containing 1 to 3 carbon atoms; $R^2$ is —$NH_2$, —NHCHO, —NHCONH$_2$, —OH, —OCH$_3$, or oxo; $R^3$ is —H or lower alkyl containing 1 to 3 carbon atoms and the pharmaceutically acceptable salts thereof.

A preferred group of compounds and chemical intermediates of the present invention is represented by formula (I) wherein $R^1$ is —H or methyl; $R^2$ is —$NH_2$, —NHCHO, —NHCONH$_2$, —OH, —OCH$_3$ or oxo; and $R^3$ is —H or ethyl and the pharmaceutically acceptable salts thereof.

A preferred group of useful chemical intermediates of the present invention is represented by formula (I) wherein $R^1$ is methyl; $R^2$ is —$NH_2$, —NHCHO or —OH; and $R^3$ is —H or ethyl.

A preferred group of anti-inflammatory and analgesic compounds of the present invention is represented by formula (I) wherein $R^1$ is —H; $R^2$ is —NHCONH$_2$ or oxo; $R^3$ is —H or ethyl and the pharmaceutically acceptable salts thereof.

The most preferred chemical intermediates of the present invention useful for the production of anti-inflammatory and analgesic agents are designated:
4-amino-1,8-diethyl-1,3,4,9-tetrahydropyrano[3,4-b]indole-1-acetic acid methyl ester;
1,8-diethyl-4-hydroxy-1,3,4,9-tetrahydropyrano[3,4-b]indole-1-acetic acid methyl ester;
1,8-diethyl-4-methoxy-1,3,4,9-tetrahydropyrano[3,4-b]indole-1-acetic acid methyl ester;
4-[(aminocarbonyl)amino]-1,8-diethyl-1,3,4,9-tetrahydropyrano[3,4-b]indole-1-acetic acid methyl ester;
1,8-diethyl-1,3,4,9-tetrahydro-4-oxopyrano[3,4-b]indole-1-acetic acid methyl ester;
1-ethyl-4-amino-1,3,4,9-tetrahydropyrano[3,4-b]indole-1-acetic acid methyl ester; and
1-ethyl-4-hydroxy-1,3,4,9-tetrahydropyrano[3,4-b]indole-1-acetic acid methyl ester.

The most preferred compounds of the present invention useful as anti-inflammatory and analgesic agents are designated:
4-[(aminocarbonyl)amino]-1,8-diethyl-1,3,4,9-tetrahydropyrano[3,4-b]indole-1-acetic acid compound with benzenemethanamine (1:1); and
1,8-diethyl-1,3,4,9-tetrahydro-4-oxopyrano[3,4-b]indole-1-acetic acid.

The compounds and chemical intermediates of this invention of formula (I) wherein $R^3$ is ethyl are prepared by the process of SCHEME 1,

SCHEME 1

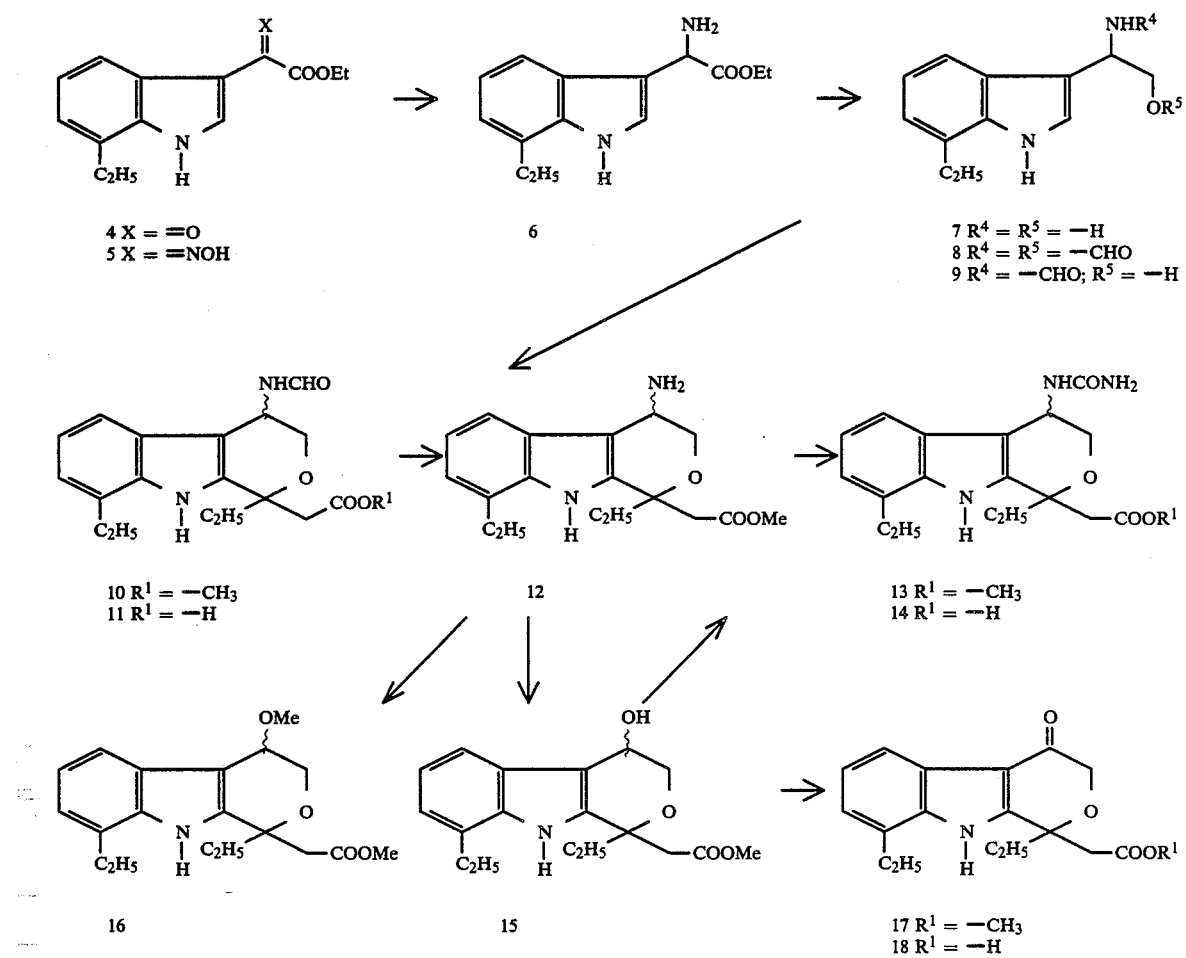

4 X = =O
5 X = =NOH

6

7 R⁴ = R⁵ = —H
8 R⁴ = R⁵ = —CHO
9 R⁴ = —CHO; R⁵ = —H

10 R¹ = —CH₃
11 R¹ = —H

12

13 R¹ = —CH₃
14 R¹ = —H

16

15

17 R¹ = —CH₃
18 R¹ = —H

The detailed process for the production of compounds 4 to 18 in SCHEME 1 is disclosed in Examples 1 to 5 herein below. The same procedure was used for the production of compounds of formula (I) wherein $R^3$ is hydrogen. SCHEME 1 was extended to provide an alternate procedure for the production of anti-inflammatory and analgesic compounds previously disclosed in Katz et al, U.S. Ser. No. 838,510, filed Mar. 11, 1986 now U.S. Pat. No. 4,670,462. Specifically, the versatile intermediate compound 15 (without the 8-ethyl group) was reacted with benzyl magnesium bromide to produce the known useful anti-inflammatory compound 4-benzyl-1-ethyl-1,3,4,9-tetrahydropyrano[3,4-b]indole-1-acetic acid. This process is disclosed in Example 6 herein below. The intermediate compound 15 was also reacted with trimethylallylsilane to produce the known useful anti-inflammatory compound 1,8-diethyl-1,3,4,9-tetrahydro-4-(2-propenyl)-pyrano[3,4-b]indole-1-acetic acid. The process is disclosed in Example 7.

Referring to SCHEME 1, the formation of the 4-substituted pyrano[3,4-b]indole acetic acid system was achieved by the condensation of the β-formamidotryptophol 9 with the enol methyl ether of methyl propionyl acetate to give 4-formamidopyrano[3,4-b]indole acetic acid methyl ester, 10. The required intermediate, β-formamidotryptophol 9 was prepared from the 7-ethylindole-3-glyoxylate 4 by conversion to oxime 5 and successive reductions to aminoester 6 and β-aminotryptophol 7. The β-aminiotryptophol 7 was exhaustively formylated to produce O,N-diformyltryptophol 8.

The β-formamidotryptophol 9 was obtained from the O,N-diformyltryptophol 8 by selective hydrolysis, and reacted with the enol methyl ether of methyl propionyl acetate in the presence of boron trifluoride etherate to give a 62.3% yield of the 4-formamidopyrano[3,4-b]indole acetic acid methyl ester, 10, as a 1:1 mixture of diastereomers. After hydrolysis to the acids 11, they were separated into the pure diastereomers by reverse phase chromatography. Hydrolysis of the formamidoesters 10 afforded aminoesters 12 which, on reaction with potassium cyanate, afforded the 4-ureidoesters 13 which were separated into the individual diastereomers by reverse phase chromatography.

The chemical behavior of the very versatile chemical intermediate 4-aminopyrano[3,4-b]indole acetic acid methyl ester 12 was investigated and resulted in the discovery of an unusual route to 4-ureido- and 4-oxopyrano[3,4-b]indole acetic acid. When the 4-amino derivative 12, as a 1:1 diastereomeric mixture, was treated with paraformaldehyde in aqueous tetrahydrofuran at reflux for 1 hour, an 80.5% yield of 4-hydroxypyrano[3,4-b]indole acetic acid ester 15 was obtained as a 19:1 mixture of diastereomers.

When the 4-aminopyrano[3,4-b]indole acetic acid methyl ester 12 was treated with aqueous formaldehyde in methanol, an 80% yield of 4-methoxypyrano[3,4-b]indole acetic acid methyl ester 16 was obtained as an 8.5:1 diastereomeric mixture.

Oxidation of 4-hydroxypyrano[3,4-b]indole acetic acid methyl ester 15 with manganese dioxide, followed by hydrolysis, afforded 4-oxopyrano[3,4-b]-indole acetic acid 18. When 15 was treated with urea in acidified aqueous tetrahydrofuran, a quantitative conversion to 4-ureidopyrano[3,4-b]indole acetic acid methyl ester 13 was achieved.

DETAILED DESCRIPTION OF THE INVENTION

The term "lower alkyl" as used herein represents straight chain alkyl radicals containing 1 to 3 carbon atoms and branched chain alkyl radicals containing three carbon atoms and includes methyl, ethyl, propyl and isopropyl.

The compounds of formula (I) form salts with suitable pharmaceutically acceptable inorganic and organic bases. These derived salts possess the same activities as the parent acid and are included within the scope of this invention. The acid of formula (I) is transformed in excellent yield into the corresponding pharmaceutically acceptable salts by neutralization of said acid with the appropriate inorganic or organic base. The salts are administered in the same manner as the parent acid compounds. Suitable bases to form these salts are set forth in Katz et al, U.S. Ser. No. 838,510, filed Mar. 11, 1986 now U.S. Pat. No. 4,670,462.

The transformations to the salts can be carried out by a variety of methods fully described in Katz et al, U.S. Ser. No. 838,510, filed Mar. 11, 1986 now U.S. Pat. No. 4,670,462.

Included in the present invention are the diastereoisomers wherein the 4-substituent is either cis or trans to the acetic acid chain at position one.

Also included in this invention are the optical isomers of the compounds of formula (I) which result from asymmetric centers, contained therein. Such isomers can be obtained in substantially pure form by classical separation techniques and by sterically controlled synthesis.

The anti-inflammatory activity of the compounds of the present invention was assessed against Freund's complete adjuvant-induced hindpaw edema in rats and the results are collected in Table 1. At 25 mg/kg/day, 1,8-diethyl-1,3,4,9-tetrahydro-4-oxopyrano[3,4-b]indole-1-acetic acid showed a 20.8% anti-inflammatory effect, whereas 1,8-diethyl-1,3,4,9-tetrahydropyrano[3,4-b]indole-1-acetic acid (etodolac) at the same dose showed a 64.3% anti-inflammatory effect. 4-[(Aminocarbonyl)amino]-1,8-diethyl-1,3,4,9-tetrahydropyrano[3,4-b]indole-1-acetic acid benzylamine salt exhibited 36.5% ($p<0.05$) anti-inflammatory activity at a dose of 69.6 mg/kg/day, calculated as the free acid. This effect was equal to that observed with 10 mg/kg/day etodolac, but significantly less ($p<0.05$) than that obtained with 25 mg/kg/day etodolac. The 4-[(aminocarbonyl)amino]-1,8-diethyl-1,3,4,9-tetrahydropyrano[3,4-b]indole-1-acetic acid benzylamine salt was a 2.4:1 mixture of diastereomers and at the dose used the individual diastereomers were administered at doses of 20.47 and 49.13 mg/kg.

ANTI-INFLAMMATORY ACTIVITY

Male Sprague-Dawley rats, weighing 180–200 g, were injected intradermally in the left hindpaw with 0.1 mL Freund's complete adjuvant (FCA; 0.5 mg killed and dried *Mycobacterium butyricum* suspended in 0.1 mL mineral oil). Test compounds or vehicle control (0.5% Tween 80 in distilled water) were administered by gastric lavage immediately before the FCA injection (day 0) and 24 and 48 hours after the FCA (days 1 and 2). The volume of the injected hindpaw was measured both before the FCA injection and 24 hours after the last drug administration (day 3) by means of a plethysmometer (Buxco Electronics, Sharon, CT). The hindpaw edema volume represents the difference between the volumes on days 0 and 3. Statistical comparisons were performed using the unpaired t test with significance achieved at the $p<0.05$ level.

Further details of this pharmacologic test are described in Katz et al, U.S. Ser. No. 838,510, filed Mar. 11, 1986, now U.S. Pat. No. 4,670,462 under the heading ANTI-INFLAMMATORY ACTIVITY.

TABLE 1

| Compound | Dose mg/kg/day | (n) | Hindpaw edema volume (mL ± S.E.M.) | Mean % Inhibition |
|---|---|---|---|---|
| vehicle | — | 10 | 1.54 ± 0.16 | — |
| etodolac | 25 | 10 | 0.55 ± 0.05** | 64.3 |
| 1,8-diethyl-1,3,4,9-tetrahydro-4-oxopyrano-[3,4-b]indole-1-acetic acid | 25 | 10 | 1.22 ± 0.15 † † | 20.8 |
| vehicle | — | 10 | 2.41 ± 0.31 | — |
| etodolac | 10 | 10 | 1.47 ± 0.12* † | 39.0 |
| etodolac | 25 | 10 | 1.09 ± 0.08** | 54.8 |
| 4-[(aminocarbonyl)amino]-1,8-diethyl-1,3,4,9-tetrahydropyrano[3,4-b]indole-1-acetic acid benzylamine salt$^a$ | 69.6 | 10 | 1.53 ± 0.18* | 36.5 |

*$p<0.05$
**$p<0.01$ relative to vehicle control.
† $p<0.05$
† † $p<0.01$ relative to 25 mg/kg etodolac.
$^a$This compound was administered as the benzylamine salt at 100 mg/kg, equivalent to 69.6 mg/kg of the free acid.

The lack of side effects associated with the compounds of this invention are demonstrated by standard acute toxicity tests as described by R. A. Turner in "Screening Methods in Pharmacology, " Academic Press, New York and London, 1965, pp 152–163, and by prolonged administration of the compound to warm-blooded animals.

When the compounds of this invention are employed as anti-inflammatory and analgesic agents in warm-blooded animals, they are administered orally, alone or in dosage forms, i.e., capsules or tablets, combined with pharmacologically acceptable excipients, such as starch, milk sugar and so forth, or they are administered orally in the form of solutions in suitable vehicles such as vegetable oils or water. The compounds of this invention may be administered orally in sustained release dosage form or transdermally in ointments or patches. The compounds of this invention may also be administered in the form of suppositories.

The dosage of the compounds of formula (I) of this invention will vary with the particular compound chosen and form of administration. Furthermore, it will vary with the particular host under treatment. Generally, the compounds of this invention are administered at a concentration level that affords efficacy without any deleterious side effects. These effective anti-inflammatory and analgesic concentration levels are usually obtained within a therapeutic range of 1.0 µg to 500 mg/kg per day, with a preferred range of 1.0 µg to 100 mg/kg per day. The preferred anti-inflammatory dose range is 1 mg to 20 mg/kg b.i.d. The preferred analgesic dose range is 1 µg to 4 mg/kg b.i.d.

The compounds of this invention may be administered in conjunction with nonsteroid anti-inflammatory drugs such as acetaminophen, ibuprofen and aspirin and/or with opiate analgesics such as codeine, oxycodone and morphine together with the usual doses of caffeine. When used in combination with other drugs, the dosage of the compounds of the present invention is adjusted accordingly.

The compounds of the present invention also possess antipyretic activity.

The following examples further illustrate this invention.

EXAMPLE 1

4-Amino-1,8-diethyl-1,3,4,9-tetrahydropyrano[3,4-b]indole-1-acetic Acid Methyl Ester 12

Step (a) Preparation of 7-Ethyl-α-oxo-1H-indole-3-acetic Acid Ethyl Ester 4

To a solution of 7-ethylindole (51 g, 0.35 mol) in dry ether (350 mL) at 0° C. was added dropwise, a solution of oxalyl chloride (89.9 g, 0.7 mol) in ether (150 mL). The mixture was stirred for 2 hours at 0° C. then the ether was removed in vacuo and absolute ethanol (500 mL) was added at 0° C. After stirring for 15 hours, ethanol was removed in vacuo and the residue was triturated with ether and recrystallized from hot ethanol to give the product (60 g, 70%), m.p. 152°-154° C.

Anal. Calcd. for $C_{14}H_{15}NO_3$: C 68.55; H 6.17; N 5.71. Found: C 68.35; H 6.06; N 5.62.

Step (b) Preparation of 7-Ethyl-α-(hydroxyimino)-1H-indole-3-acetic Acid Ethyl Ester 5

Solutions of sodium acetate (43.7 g, 0.53 mol) in water (100 mL) and hydroxylamine hydrochloride (37 g, 0.53 mol) in water (100 mL) were added to 7-ethyl-α-oxo-1H-indole-3-acetic acid ethyl ester 4 (17.4 g, 0.07 mol), in ethanol (250 mL) and the mixture was heated at reflux for 12 hours. The ethanol was removed by distillation and the resultant precipitate was filtered and recrystallized from hot ethanol to give the product (13.8 g, 75%), m.p. 167°-169° C. as a mixture of isomers.

Anal. Calcd. for $C_{14}H_{16}N_2O_3$: C 64.60; H 6.20; N 10.76. Found: C 64.57; H 6.11; N 10.55.

Step (c) Preparation of α-Amino-7-ethyl-1H-indole-3-acetic Acid Ethyl Ester 6

To 7-ethyl-α-(hydroxyimino)-1H-indole-3-acetic acid ethyl ester 5 (7.3 g, 0.028 mol) in ethanol (200 mL) was added concentrated HCl (3 mL) and 10% Pd/C (1.0 g). The mixture was hydrogenated at 40 p.s.i. for 4 hours at 22° C. The catalyst and the solvent were removed and the residue was dissolved in water. After washing with methylene chloride, the aqueous phase was basified with 20% sodium hydroxide. The precipitated product, α-amino-7-ethyl-1H-indole-3-acetic acid ethyl ester 6 (6.0 g, 87%), was filtered, washed with water and dried. A sample recrystallized from hot ethanol had m.p. 120°-122° C.

Step (d) Preparation of β-Amino-7-ethyl-1H-indole-3-ethanol 7

α-Amino-7-ethyl-1H-indole-3-acetic acid ethyl ester 6 (4.9 g, 0.02 mol) in THF (50 mL) was added to $LiAlH_4$ (2.3 g, 0.06 mol) in THF (25 mL) and the mixture was refluxed for 2 hours to give β-amino-7-ethyl-1H-indole-3-ethanol 7 (3.5 g, 85.7%). A sample recrystallized from ethyl acetate-hexane had m.p. 84°-86° C.

Step (e) Preparation of Formic Acid 7-Ethyl-β-(formylamino)-1H-indole-3-ethanol Ester 8

β-Amino-7-ethyl-1H-indole-3-ethanol 7 (48 g, 0.23 mol) and formic-acetic anhydride [prepared from acetic anhydride (320 mL) and 88% formic acid (135 mL)] were combined and kept at 22° C. for 16 hours, then poured onto ice and extracted with ethyl acetate. The extracts were washed with saturated $NaHCO_3$ solution, dried and evaporated to give formic acid 7-ethyl-β-(formylamino)-1H-indole-3-ethanol ester 8 (58.6 g, 98%). A sample recrystallized from ethyl acetate-hexane had m.p. 159°-161° C.

IR (KBr): 3310 cm$^{-1}$ (NH), 1735 cm$^{-1}$ (O—COH), 1650 cm$^{-1}$ (N—COH);

$^1$H-NMR (DMSO): δ1.28 (t, J=7, 3H), 2.9 (q, J=7, 2H), 4.5 (m, 2H), 5.6 (m, 1H), 6.9 (d, 2H), 7.45 (m, 2H), 8.3 (m, 3H), 10.95 (m, 1H);

Anal. Calcd. for $C_{14}H_{16}N_2O_3$: C 64.60; H 6.20; N 10.76. Found: C 64.14; H 6.22; N 10.75.

Step (f) Preparation of 7-Ethyl-β-(formylamino)-1H-indole-3-ethanol 9

Formic acid 7-ethyl-β-(formylamino)-1H-indole-3-ethanol ester 8 (50 g, 0.19 mol), methanol (800 mL) and 5% aqueous $K_2CO_3$ (800 mL) were heated at 55° C. for 2 hours. The mixture was cooled to 22° C. and the precipitate was filtered, washed with water and dried in vacuo to afford 7-ethyl-β-(formylamino)-1H-indole-3-ethanol 9 (39.7 g, 90%). A sample recrystallized from ethanol had m.p. 195°-197° C.

$^1$H NMR (DMSO): δ1.28 (t, J=7, 3H), 2.88 (q, J=7, 2H), 3.5 (br s, 1H), 3.78 (d, J=6, 2H), 5.3 (t, J=6, 1H), 6.8-7.8 (m, 4H), 8.3 (s, 1H), 11.06 (br s, 1H);

Anal. Calcd. for $C_{13}H_{16}N_2O_2$: C 67.22; H 6.94; N 12.06. Found: C 67.21; H 6.97; N 12.20.

Step (g) Preparation of 1,8-Diethyl-4-formylamino-1,3,4,9-tetrahydropyrano[3,4-b]indole-1-acetic Acid Methyl Ester 10

To a mixture of 7-ethyl-β-(formylamino)-1H-indole-3-ethanol 9 (5 g, 0.021 mol) (50 mL) and the enol methyl ether of methyl propionyl acetate (50 mL) in methylene chloride was added boron trifluoride etherate (1 mL) under nitrogen. After stirring at 22° C. for 24 hours, the mixture was concentrated in vacuo and chromatographed on silica gel. Elution with 2:1 hexane-ethyl acetate (2 L) afforded (4.5 g, 62.3%), of 1,8-diethyl-4-formylamino-1,3,4,9-tetrahydropyrano[3,4-b]indole-1-acetic acid methyl ester 10, m.p. 154°-156° C., as a 1:1 mixture of diastereomers.

Step (g) Preparation of 1,8-Diethyl-4-formylamino-1,3,4,9-tetrahydropyrano[3,4-b]indole-1-acetic Acid 11

1,8-Diethyl-4-formylamino-1,3,4,9-tetrahydropyrano[3,4-b]indole-1-acetic acid methyl ester 10 (3.5 g, 0.01 mol), methanol (80 mL), and $K_2CO_3$ (1.7 g, 0.012 mol) in water (10 mL) were heated at reflux under nitrogen for 8 hours, then concentrated in vacuo, diluted with water and extracted with ether. Acidification of the aqueous phase with 1N HCl and extraction with ethyl acetate gave a diastereomeric mixture of 1,8-diethyl-4-formylamino-1,3,4,9-tetrahydropyrano[3,4-b]indole-1-acetic acid 11 (2.2 g, 66.6%). The pure diastereomers were separated by reverse phase chromatography (C$_{18}$ silica gel, 30% acetonitrile and 70% 1 mM KH$_2$PO$_4$, pH 3.0) to give 500 mg of the more polar "Isomer A", and 430 mg of the less polar "Isomer B".

Isomer "A"; IR(KBr) 3420, 3320, 1705, 1600 cm$^{-1}$; MS m/e 330;

Anal. Calcd. for C$_{18}$H$_{22}$N$_2$O$_4$: C 65.44; H 6.71; N 8.48. (Isomer A) Found: C 65.37; H 6.55; N 8.48.

Isomer "B": IR(KBr) 3370, 3320, 1725, 1620 cm$^{-1}$; MS m/e 330;

Anal. Calcd. for C$_{18}$H$_{22}$N$_2$O$_4$: C 65.44; H 6.71; N 8.48. (Isomer B) Found: C 65.34; H 6.64; N 8.43.

Step (h) Preparation of 4-Amino-1,8-diethyl-1,3,4,9-tetrahydropyrano[3,4-b]indole-1-acetic Acid Methyl Ester 12

1,8-Diethyl-4-formylamino-1,3,4,9-tetrahydropyrano[3,4-b]indole-1-acetic acid methyl ester 10 (5.5 g, 0.01 mol) in 1N methanolic HCl (4.2 mL) and methanol (18 mL) was stirred at 25° C. for 72 hours, then concentrated in vacuo, diluted with water and extracted with ethyl acetate. The aqueous phase was basified with concentrated NaHCO$_3$ solution and extracted with ether to afford the product (1.58 g, 50%), m.p. 230° C. (dec.) after recrystallization from ether.

$^1$H NMR (CDCl$_3$) δ0.9 (m, 3H), 1.38 (t, J=7, 3H), 2.12 (m, 2H), 3.0 (m, 4H), 3.8 (d, 2H), 4.0 (s, 3H), 6.9-7.8 (m, 3H), 9.5 (m, 1H).

Anal. Calcd. for C$_{18}$H$_{24}$N$_2$O$_3$: C 68.33; H 7.65; N 8.85. Found: C 68.07; H 7.52; N 8.79.

EXAMPLE 2

1,8-Diethyl-4-methoxy-1,3,4,9-tetrahydropyrano[3,4-b]indole-1-acetic Acid Methyl Ester 16

To a solution of 4-amino-1,8-diethyl-1,3,4,9-tetrahydropyrano[3,4-b]indole-1-acetic acid methyl ester 12 (prepared in Example 1) (1.0 g, 0.003 mol) in methanol (25 mL) was added 37% aqueous formaldehyde (7.5 mL) and the mixture was heated at reflux for 30 minutes, and concentrated in vacuo. The residue was dissolved in ethyl acetate and the solution was washed with 10% aqueous NaHCO$_3$ and brine. After drying and concentrating the ethyl acetate solution, the residue was chromatographed on silica gel. Elution with petroleum ether:ethyl acetate (7:3) gave the product (795 mg, 80%), m.p. 114°-115° C. (ethyl acetate/hexane) with a diastereomeric ratio of 8.5:1, determined by analytical HPLC.

IR(KBr) 3400, 1700 cm$^{-1}$;
MS, m/e 331 (M$^+$), 299 (M$^+$—CH$_3$OH);
Anal. Calcd. for C$_{19}$H$_{25}$NO$_4$: C 68.86; H 7.60; N 4.23. Found: C 68.74; H 7.53; N 4.23.

EXAMPLE 3

4-[(Aminocarbonyl)amino]-1,8-diethyl-1,3,4,9-tetrahydropyrano[3,4-b]indole-1-acetic Acid Compound with Benzenemethanamine (1:1)

Step (a) Preparation of 4-[(Aminocarbonyl)amino]-1,8-diethyl-1,3,4,9-tetrahydropyrano[3,4-b]indole-1-acetic Acid Methyl Ester 13

To a solution of 4-amino-1,8-diethyl-1,3,4,9-tetrahydro[3,4-b]indole-1-acetic acid methyl ester 12 (prepared in Example 1) (1.10 g, 3.48 mmol) in ethanol (20 mL), stirred at room temperature under nitrogen, was added aqueous 1N HCl (6.96 mL) followed by potassium cyanate (0.565 g, 6.96 mmol) dissolved in a little water. After 2 hours the ethanol was removed in vacuo and the residue was extracted with ethyl acetate. Drying (MgSO$_4$) and flash chromatography (1% MeOH in EtOAc eluent) afforded the product (0.714 g, 75%) as a mixture of diastereomers which were separated by reverse phase chromatography (C$_{18}$ silica gel; 30% acetonitrile in water). The less polar Isomer A (190 mg) had m.p. 179.5°-180.5° C. (methylene chloride-petroleum ether).

$^1$H NMR (CDCl$_3$): δ0.82 (t, 3H), 1.38 (t, 2H), 2.15 (m, 2H), 2.9 (m, 4H), 3.62 (s, 3H), 4.02 (m, 2H), 4.3 (m, 2H), 4.8 (m, 1H), 5.0 (m, 1H), 6.9-7.7 (m, 3H), 9.05 (br s, 1H);

IR(KBr): 3400 (NH), 1720 (COOMe), 1650 (NHCONH$_2$);

MS: 359 (M$^+$), 299 (M$^+$—CH$_3$OH, CO), 270 (M—C$_2$H$_5$);

Anal. Calcd. for C$_{19}$H$_{25}$N$_3$O$_4$: C 63.49; H 7.01; N 11.69. Found: C 63.24; H 6.95; N 12.16.

The more polar Isomer B, (100 mg) m.p. 166°-168° C., had the following spectral characteristics.

$^1$H NMR (CDCl$_3$): δ0.9 (t, 3H), 1.36 (t, 3H), 2.0 (m, 2H), 2.9 (m, 4H), 3.7 (s, 3H), 4.0 (m, 2H), 4.2 (br m, 2H), 5.1 (m, 2H), 6.9-7.6 (m, 3H), 9.15 (br s, 1H);

IR(KBr) 3410 (NH), 1735 (COOMe), 1655 cm$^{-1}$ (NHCONH$_2$);

MS: 359 (M$^+$), 299 (M$^+$—CH$_2$OH, CO), 270 (M—C$_2$H$_5$);

Anal. Calcd. for C$_{19}$H$_{25}$N$_3$O$_4$: C 63.49; H 7.01; N 11.69. Found: C 63.38; H 6.71; N 11.17.

Step (b) Preparation of 4-[(Aminocarbonyl)amino]-1,8-diethyl-1,3,4,9-tetrahydropyrano[3,4-b]indole-1-acetic Acid Compound with Benzenemethanamine (1:1) 14

A solution of a diastereomeric mixture of 4-[(aminocarbonyl)amino]-1,8-diethyl-1,3,4,9-tetrahydropyrano[3,4-b]indole-1-acetic acid methyl ester (2.34 g, 6.51 mmol) and potassium carbonate (1.07 g, 7.8 mmol) in methanol (62 mL) and water (7.8 mL) was refluxed for 18 hours under nitrogen. The mixture was concentrated in vacuo, diluted with water, and washed with ether (2×20 mL). The aqueous phase was acidified to pH 2 with 1N HCl and extracted with ethyl acetate. The extracts were dried (MgSO$_4$) and evaporated in vacuo to give a foam (2.4 g).

A portion (1.7 g, 5.18 mmol) was stirred with ether (17.9 mL) and just enough ethyl acetate to cause dissolution. To the stirred solution was added benzylamine (555 mg, 5.18 mmol); the precipitated benzylamine salt was filtered, and washed with ether to give, after drying, 1.9 g of product (87%), shown to be a 2.4:1 mixture of diastereomers by integration of the triple NMR signals at 0.70 and 0.81 generated by the 1-ethyl group.

$^1$H NMR (DMSO-d$_6$, 400 MHz): δ0.70 (t, J=7.2), 0.81 (t, J=7.2), 1.23 (t, 3H, J=7.4), 1.9-2.16 (m), 2.49-2.56 (m), 3.6-3.72 (m), 3.89-4.0 (m), 4.78 (m), 4.84-5.0 (m), 5.4 (m), 5.52 (m), 5.84 (m), 6.03 (m), 6.86 (m), 7.24-7.42 (m), 11.0 (m), 11.26 (m);

Anal. Calcd. for C$_{25}$H$_{32}$N$_4$O$_2$: C 66.35; H. 7.13; N 12.38. Found: C 66.25; H 7.05; N 12.25.

EXAMPLE 4

4-[(Aminocarbonyl)amino]-1.8-diethyl-1,3,4,9-tetrahydropyrano[3,4-b]indole-1-acetic Acid Methyl Ester

Step (a) Preparation of 1,8-Diethyl-4-hydroxy-1,3,4,9-tetrahydropyrano[3,4-b]indole-1-acetic Acid Methyl Ester 15

To a solution of 4-amino-1,8-diethyl-1,3,4,9-tetrahydropyrano[3,4-b]indole-1-acetic acid methyl ester (prepared in Example 1) (1.5 g, 0.0047 mol) in THF (5 mL) was added water (5 mL) and paraformaldehyde (0.5 g). The mixture was heated at reflux for 1 hour, then concentrated in vacuo and the residue extracted with ether. The ether extracts were washed with saturated NaHCO$_3$ solution, brine, and dried and concentrated in vacuo. Elution from a silica gel column with a 7:3 hexane:ethyl acetate mixture gave the product (1.2 g, 80.5%), m.p. 117°–118° C. (ether/hexane). Analytical HPLC showed that the product consisted of two diastereomers in a ratio of 19:1.

IR(KBr): 3400, 3280, 1720 cm$^{-1}$;

MS: m/e 317 (M+), 299 (M+—H$_2$O);

Anal. Calcd. for C$_{18}$H$_{23}$NO$_4$: C 68.12; H 7.30; N 4.41. Found: C 68.06; H 7.29; N 4.40.

Step (b) Preparation of 4-[(Aminocarbonyl)amino]-1,8-diethyl-1,3,4,9-tetrahydropyrano[3,4-b]indole-1-acetic Acid Methyl Ester To a solution of 1,8-diethyl-4-hydroxy-1,3,4,9-tetrahydropyrano[3,4-b]indole-1-acetic methyl ester (100 mg, 0.3 mmol) in tetrahydrofuran (3 mL) was added urea (20 mg, 0.35 mmol) in water (0.5 mL) and aqueous 1N HCl (0.2 mL). The mixture was heated at 55° C. for 1 hour. TLC analysis showed the absence of starting material and the appearance of a spot having the same Rf value as authentic 4-[(aminocarbonyl)amino]-1,8-diethyl-1,3,4,9-tetrahydropyrano]3,4-b]indole-1-acetic acid methyl ester. HPLC analysis indicated a 1:1 mixture of diastereomers and mass spectral analysis showed a fragmentation pattern identical to material prepared in Example 3, Step (a).

EXAMPLE 5

1,8-Diethyl-1,3,4,9-tetrahydro-4-oxopyrano[3,4-b]indole-1-acetic Acid

Step (a) Preparation of 1,8-Diethyl-1,3,4,9-tetrahydro-4-oxopyrano[3,4-b]indole-1-acetic Acid Methyl Ester 17

1,8-Diethyl-4-hydroxy-1,3,4,9-tetrahydro[3,4-b]indole-1-acetic acid methyl ester 15 (2.5 g, 8.0 mmol) was added in one portion to a suspension of manganese dioxide (15 g) in 150 mL of ether. The solution was allowed to stir at room temperature for 16 hours, after which time an extra 2 g of manganese dioxide was added and the mixture allowed to stir an additional 2 hours to complete the reaction. The manganese dioxide was removed by filtration through celite, and the pad was washed with 500 mL of CH$_2$Cl$_2$. The solvent was concentrated in vacuo to provide 2.2 g of crude solid, which was recrystallized from hot EtOAc-hexane to yield 1.45 g of colorless crystals, m.p. 192°–193° C. Concentration of the mother liquor provided a second crop (210 mg) of crystals for a total yield of 64%. $^1$H NMR (400 MHz, DMSO-d$_6$): δ 7.77 (d, J=7, 1H), 7.14 (t, J=7, 1H), 7.07 (d, J=7, 1H), 4.27 (d, J=17, 1H), 4.21 (d, J=17, 1H), 3.52 (s, 3H), 3.31 (s, 2H), 2.90 (m, 2H), 2.23 (m, 1H), 1.88 (m, 1H), 1.25 (t, J=7.5, 3H), 0.81 (t, J=7, 3H);

IR(KBr): 1735 (C=O), 1620 cm$^{-1}$(C=O);

MS: m/e 315 (27.5, M+), 286 (79.9, M—C$_2$H$_5$), 242 (100, M—CH$_2$COOH$_3$);

Anal. Calcd. for C$_{18}$N$_{21}$NO$_4$: C 68.55; H, 6.71; N 4.44 Found: C 68.77; H 6.51; N 4.64.

Step (b) Preparation of 1,8-Diethyl-1,3,4,9-tetrahydro-4-oxopyrano[3,4-b]indole-1-acetic Acid 18

1,8-Diethyl-1,3,4,9-tetrahydro-4-oxopyrano[3,4-b]indole-1-acetic acid methyl ester 17 (1.5 g, 4.8 mmol) was suspended in 30 mL of MeOH and a solution of K$_2$CO$_3$ (3.5 g) in 30 mL of H$_2$O was added. The mixture was heated to reflux, upon which the solution became homogeneous. After refluxing for 2 hours, the solution was cooled to room temperature, and the MeOH removed in vacuo. The aqueous solution was made acidic with 6N HCl, and the resulting cloudy solution was extracted with ether (2×50 mL). The ether layer was washed with 25 mL of saturated NaCl solution, then dried over MgSO$_4$. The MgSO$_4$ was removed and the ether was evaporated. Hexane was gradually added until a slight turbidity was observed. The solution was left at 0° C. overnight and the resultant solid was collected by filtration and dried to provide analytically pure product (1.31 g, 93%), m.p. 200°–202° C.

$^1$H NMR (400 MHz, DMSO-d$_6$): δ 11.43 (br s, 1H), 10.84 (br s, 1H), 7.77 (d, J=7, 1H), 7.14 (t, J=7, 1H), 7.06 (d, J=7, 1H), 4.28 (d, J=17, 1H), 4.21 (d, J=17, 1H ), 3.19 (d, J=15, 1H), 2.89 (q, J=7.5 2H), 2.81 (d, J=15, 1H), 2.23 (m, 1H), 2.01 (m, 1H), 1.24 (t, J=7.5, 3H), 0.81 (t, J=7.4, 3H);

IR (KBr): 3520 (OH), 1715 (C=O), 1620 cm$^{-1}$(C=O);

MS: m/e 301 (59.8, M+), 272 (100, M+—C$_2$H$_5$), 242 (97.9, M—CH$_2$—COOH);

Anal. Calcd. for C$_{17}$H$_{19}$NO$_4$: C 67.76; H, 6.36; N 4.65. Found: C 67.70; H 6.06; N 4.52.

EXAMPLE 6

4-Benzyl-1-ethyl-1,3,4,9-tetrahydropyrano[3,4-b]indole-1-acetic Acid

Step (a) Preparation of 4-Amino-1-ethyl-1,3,4,9-tetrahydropyrano[3,4-b]indol-1-acetic Acid Methyl Ester Starting with an equivalent amount of indole and carrying out the Steps (a) to (f) and Step (h) in Example 1, the product having the following physical properties was obtained.

NMR (CDCl$_3$/TMS): δ 0.85 (2t, 3H), 2.0 (m, 5H, 2.8–3.2 (m, 2H), 3.8 (2s, 3H), 4.1 (m, 2H), 7–7.8 (m, 4H), 8.8–9.2 (2s, 1H).

Step (b) Preparation of 1-Ethyl-4-hydroxy-1,3,4,9-tetrahydropyrano[3,4-b]indole-1-acetic Acid Methyl Ester To a solution of 4-amino-1-ethyl-1,3,4,9-tetrahydropyrano[3,4-b]indole-1-acetic acid methyl ester (6 g, 0.020 mol) in 50 mL THF was added 50 mL of H$_2$O and paraformaldehyde (5 g) and the solution was heated at reflux for 2 hours under nitrogen. It was then cooled, concentrated in vacuo, and diluted with ethyl acetate. The ethyl acetate layer was washed with saturated sodium bicarbonate solution, brine, dried and concentrated in vacuo. The residue was purified by flash chromatography eluting with hexane to give a white solid (4 g, 66.4%) m.p. 86°–90° C.

NMR (CDCl$_3$/TMS): δ 0.9 (2, 3H), 1.5 (s), 1.8–2.2 (m, 3H), 2.8–3.1 (m, 2H), 3.8 (2s, 3H), 4 (m, 2H), 4.8 (m, 1H), 7–7.7 (m, 4H), 9–9.2 (2s, 1H).

Step (c) Preparation of 4-Benzyl-1-ethyl-1,3,4,9-tetrahydropyrano[3,4-b]indole-1-acetic Acid Methyl Ester To a solution of 1-ethyl-4-hydroxyl-1,3,4,9-tetrahydropyrano[3,4-b]indole-1-acetic acid methyl ester (1 g, 3.6 mmol) in 60 mL of dry methylene chloride at −78° C. under nitrogen was added TiCl4 in one portion and then after ~10 minutes, a solution of banzyl magnesium bromide in ether was added in one portion and the reaction mixture was allowed to stir at −78° C. for ~30 minutes. The reacton was quenched with methanol (3 mL) at −78° C. and then poured into water (10 mL). The two layers were separated and the aqueous layer was then extracted with methylene chloride (2×100 mL), dried over magnesium sulfate and concentrated in vacuo. The crude product was passed through a pad of silica gel, eluting with 10% EtOAc in hexane to give 0.67 g (51.5%) of the product as an oil, which had isomer ratio of 75:25 by HPLC.

NMR (CDCl3/TMS): δ 0.9 (t, 3H), 2.0 (m, 2H), 2.7-3.3 (m, 5H), 3.7 (s, 3H), 3.8 (m, 2H), 7-7.5 (m, 9H), 9.2 (s, 1H).

Step (d) Preparation of 4-Benzyl-1-ethyl-1,3,4,9-tetrahydropyrano[3,4-b]indole-1-acetic Acid To a solution of 4-benzyl-1-ethyl-1,3,4,9-tetrahydropyrano[3,4-b]indole-1-acetic acid methyl ester (0.67 g, 1.8 mmol) in 30 mL of ethanol was added 30 mL of 10% solution of sodium hydroxide and heated at reflux for 2 hours under nitrogen. The reaction mixture was then cooled and concentrated in vacuo, diluted with 20 mL of H2O and extracted with ether. The aqueous layer was then acidified with 2N HCl and extracted with chloroform (3×100 mL), dried over magnesium sulfate and concentrated in vacuo to give 0.516 g (80%) of the product, m.p. 142°-143° C.

516 mg of this product was recrystallized from benzene and petroleum ether to give 250 mg of the product which had isomer ratio of (10:1) by HPLC.

Another recrystallization of the product (250 mg) from hot benzene gave 115 mg of the product with isomer ratio (97.3) HPLC.

One more recrystallization of 115 mg of the product from benzene gave the isomer ratio (98.5:1.5) HPLC (100 mg).

NMR (CDCl3/TMS): δ 0.9 (t, 3H), 2.0 (m, 2H), 2.7-3.5 (m, 5H), 3.9 (d, 2H), 7-7.5 (m, 9H), 8.65 (s, 1H),

EXAMPLE 7

1,8-Diethyl-1,3,4,9-tetrahydro-4-(2-propenyl)-pyrano[3,4-b]indole-1-acetic Acid

To a solution of 1,8-diethyl-4-hydroxy-1,3,4,9-tetrahydropyrano[3,4-b]indole-1-acetic acid methyl ester (a 19:1 diastereomeric mixture; 1.68 g, 5.3 mmol) in tetrahydrofuran (10 mL) at −78° C., was added titanium tetrachloride (1.5 g, 7.9 mmol) and allyltrimethylsilane (0.73 g, 6.3 mmol) and the mixture was stirred for 30 minutes, then quenched by the addition of 5 mL of methanol. The mixture was poured into water (10 ml) and extracted with methylene chloride. The extracts were dried then concentrated in vacuo to give 1.7 g of an oil. It was chromatographed on silica gel; elution with hexane:ethyl acetate (9:1) gave 1,8-diethyl-1,3,4,9-tetrahydro-4-(2-propenyl)pyrano[3,4-b]indole-1-acetic acid methyl ester (1.2 g, 66.4%) as a solid, m.p. 92°-93° C. The methyl ester (1.0 g, 2.9 mmol) was dissolved in methanol (50 mL) and potassium carbonate (0.6 g, 4.4 mmol) and water (5 mL) were added. The mixture was heated at reflux under nitrogen for 8 hours, then the methanol was removed in vacuo, the residue was diluted with water and extracted with ether. The aqueous phase was acidified to pH 2 with 1N HCl and extracted with ethyl acetate to afford the crude product (0.9 g). It was chromatographed on silica gel. Elution with hexane:ethyl acetate (6:4) gave 700 mg of crude product with an isomer ratio of ~10:1 as determined by HPLC. It was purified by preparative HPLC to give 250 mg of a single isomer which was recrystallized from an ether-petroleum ether mixture to give the product (130 mg), m.p. 96°-97° C.

Anal. Calcd. for C20H25NO3: C 73.39; H 7.65; N 4.28. Found: C 73.35; H 7.70; N 4.20.

1H NMR (CDCl3) δ 0.94 (t, 3H, J=7), 1.30 (t, 3H, J=8), 2.06 (m, 2H), 2.44 (m, 1H), 2.75 (m, 3H), 2.98 (m, 1H), 3.00 (d, 1H, J=17.5), 3.10 (d, 1H, J=17.5), 3.94 (m, 2H), 5.12 (m, 2H), 5.92 (m, 1H), 7.04 (m, 2H), 7.43 (d, 1H, J=8), 8.75 (s, 1H);

MS: m/e 327 (M+), 298 (M+—C2H5).

We claim:

1. A process for producing the compounds of formula (I)

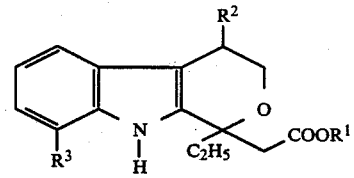

wherein R1 is lower alkyl; R2 is —NH2; and R3 is —H or lower alkyl which comprises the steps (a) reacting the compound of formula

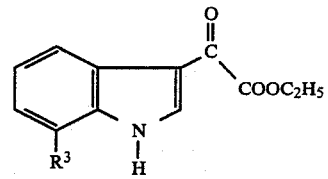

wherein R3 is as defined above with hydroxylamine hydrochloride to produce the oxime of formula

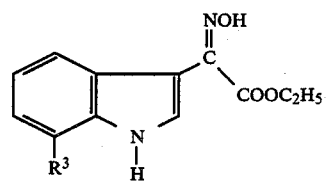

wherein R3 is a defined above (b) successively reducing the oxime group and the ethoxycarbonyl group with hydrogen and palladium on carbon catalyst and with lithium aluminium hydride respectively to produce the aminotyptophol compound of formula

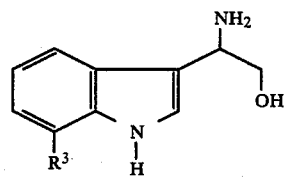

wherein R3 is as defined above (c) formylating said aminotryptophol with formic-acetic anhydride to produce the diformyl compound of formula

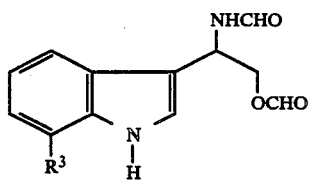

wherein R³ is as defined above
(d) selectively deformylating said diformyl compound to produce the monoformyl compound of formula

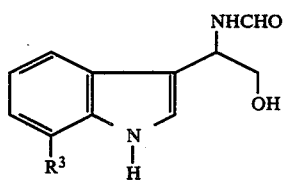

wherein R³ is as defined above
(e) reacting said monoformyl compound with the enol methyl ether of methyl propionyl acetate having the structure

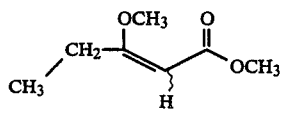

in the presence of boron trifluoride etherate to produce the 4-formamidopyrano[3,4-b]indole acetic acid methyl ester of formula

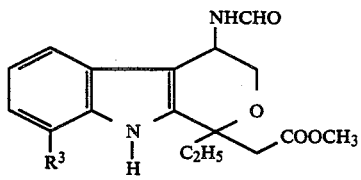

wherein R³ is as defined above and
(f) deformylating said 4-formamido compound to produce the desired compound of formula (I).

2. A process for producing the compounds of formula (I)

(I)

[structure with R², R³, COOR¹, C₂H₅]

wherein R¹ is —H, R² is —NHCONH₂, and R³ is —H or lower alkyl and the pharmaceutically acceptable salts thereof which comprises
(a) treating the compound of formula

[structure with NH₂, R³, C₂H₅, COOCH₃]

produced according to claim 1 wherein R³ is as defined above with paraformaldehyde to produce the 4-hydroxy compound of formula

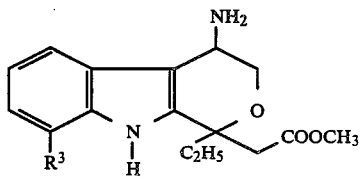

wherein R³ is as defined above and treating said 4-hydroxy compound with urea to produce, after hydrolysis, the desired compound of formula (I) or
(b) alternately treating the compound of formula

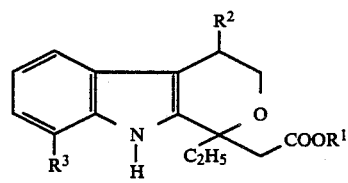

with potassium cyanate, KCNO, in the presence of mineral acid to produce, after hydrolysis, the desired compound of formula (I).

3. A process for producing the compound of formula

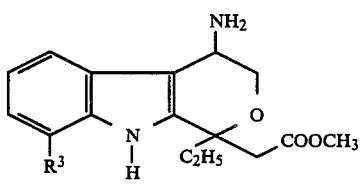

wherein R³ is —H or lower alkyl and the pharmaceutically acceptable salts thereof which comprises (a) treating the compound of the formula

[structure with NH₂, R³, C₂H₅, COOCH₃]

produced according to claim 1 wherein R³ is as defined above with paraformaldehyde to produce the 4-hydroxy compound of formula 17
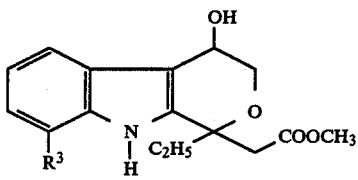
and
(b) treating the 4-hydroxy compound with benzylmagnesium bromide, benzylmagnesium chloride or benzylmagnesium iodide and hydrolyzing the ester group.
* * * * *
18
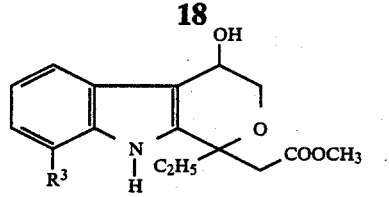
and
(b) treating the 4-hydroxy compound with benzylmagnesium bromide, benzylmagnesium chloride or benzylmagnesium iodide and hydrolyzing the ester group.
* * * * *